(12) United States Patent
Pubols et al.

(10) Patent No.: US 7,255,716 B2
(45) Date of Patent: Aug. 14, 2007

(54) METHOD AND INSTRUMENTS FOR INSERTING MODULAR IMPLANT COMPONENTS

(76) Inventors: Steven C. Pubols, 6180 Cobblestone Rd., Placerville, CA (US) 95667; Michael A. Serra, 4607 Hillwood Dr., Shingle Springs, CA (US) 95682

( * ) Notice: Subject to any disclaimer, the term of this patent is extended or adjusted under 35 U.S.C. 154(b) by 230 days.

(21) Appl. No.: 10/440,647

(22) Filed: May 9, 2003

(65) Prior Publication Data

US 2004/0127910 A1     Jul. 1, 2004

Related U.S. Application Data

(60) Provisional application No. 60/378,986, filed on May 9, 2002.

(51) Int. Cl.
*A61F 2/32* (2006.01)
(52) U.S. Cl. ................. 623/22.42; 623/22.46; 606/99
(58) Field of Classification Search ............ 606/99
See application file for complete search history.

(56) References Cited

U.S. PATENT DOCUMENTS

| 4,846,839 | A | 7/1989 | Noiles |
| 6,264,699 | B1* | 7/2001 | Noiles et al. ............ 623/23.23 |
| 6,330,845 | B1 | 12/2001 | Meulink |
| 6,361,563 | B2 | 3/2002 | Terrill-Grisoni et al. |
| 6,626,913 | B1* | 9/2003 | McKinnon et al. .......... 606/99 |
| 6,673,114 | B2 | 1/2004 | Hartdegen et al. |
| 7,044,975 | B2* | 5/2006 | Cheal et al. ............. 623/22.42 |

* cited by examiner

*Primary Examiner*—Cris Rodriguez
*Assistant Examiner*—Candice C. Stokes
(74) *Attorney, Agent, or Firm*—Pandiscio & Pandiscio

(57) ABSTRACT

An instrument is disclosed for inserting a modular implant, the instrument comprising a first end and a second end, the first end having engagement means for engaging a stem component of the modular implant, the engagement means comprising separation means for separating a body component of the modular implant and the stem component from one another so as to permit rotational positioning of the body component and the stem component relative to one another.

12 Claims, 2 Drawing Sheets

METHOD AND INSTRUMENTS FOR INSERTING MODULAR IMPLANT COMPONENTS

REFERENCE TO PENDING PRIOR PATENT APPLICATION

This patent application claims benefit of now abandoned prior U.S. Provisional Patent Application Ser. No. 60/378,986, filed May 9, 2002 by Steven C. Pubols et al. for METHOD FOR INSERTING MODULAR IMPLANT COMPONENTS, which patent application is hereby incorporated herein by reference.

FIELD OF THE INVENTION

This invention is related to modular orthopedic apparatus and methods in general, and more particularly to apparatus and methods for inserting modular implant components.

BACKGROUND OF THE INVENTION

The aim of Total Hip Arthroplasty (THA) is the reduction of pain and the restoration of function to a diseased hip joint via the substitution of engineered materials for the diseased tissue. Successful outcomes depend largely on the proper sizing, placement and orientation of the implant. Incorrect biomechanics (e.g. joint reaction forces, soft tissue balancing) can slow or prevent healing, cause gait abnormalities and lead directly to early implant failure.

There are three portions to the femoral side of a total hip prosthesis: the neck, body, and stem. In a one piece hip design, all three of these portions are a part of a solid construct. As a solid construct, the orientation of each portion with respect to one another is fixed and unchangeable. A surgeon implants one of these solid construct devices by attaching a handle or holder to the prosthesis and then driving it into a prepared opening in the bone. The orientation of the neck and stem is controlled by, and limited to, the orientation of the prepared opening in the bone.

With the invention of two-piece designs, specifically U.S. Pat. No. 4,846,839, issued to Noiles, incorporated herein by reference, and subsequently marketed and sold by DePuy, A Johnson and Johnson Company, under the "S-ROM Hip System" tradename, a surgeon is given the opportunity to independently orient the position of the implant body apart from the rotation or anteversion of the neck. In these designs, the stem and neck of the implant are a one-piece component and the body of the implant is a separate component. These devices also incorporate flutes or spines on the stems of the implant so as to provide additional resistance to rotation. These spines engage the bone during the initial few inches of insertion into the femoral canal, forcing the final location of the implant neck to be totally dependent on the initial insertion orientation of the distal stem. If the stem is fully inserted and the neck is incorrectly oriented, the entire implant must be removed, indexed, and reinserted. This iterative approach to neck placement is time consuming, damages the bone/implant interface, and results in the loss of implant stability. This problem is compounded when a bowed stem is used in place of a straight stem. The bow in the stem will follow the natural bend in femoral canal, which in turn dictates the final position of the femoral neck. Using two-piece modular implants, where the first piece is a neck with curved stem component and the second piece is the body component, a surgeon is given no choice or option for the femoral neck orientation with respect to the orientation of the bowed or curved stem.

With a three-piece modular implant, there is provided a stem component, a neck component, and a body component which are independent of one another and are independently adjustable with respect to one another. With insertion, the stem component and body component each seek a best fitting position within the femoral canal. Following insertion, the neck component can be oriented by a surgeon in order to establish optimal joint and motion mechanics.

Prior to insertion of an actual implant, the use of a mock implant or "trial" is desirable as a means of evaluating correct size and positioning. A surgeon uses the measurements taken from the trial implant so as to select the final implant components. A trial stem is generally smaller than an implant stem and is configured without spines or flutes so as to aid in the insertion and removal of the trial without damaging the bone/implant interface. When inserted into the prepared cavity in the bone, the stem component will follow the path of least resistance so long as its motion is not restricted otherwise. For this reason, it is advantageous to allow the implant stem rotational freedom with respect to the body when inserting the final implant. Although it is desirable for the stem component to be rotationally free during insertion, it is important for the stem component to be properly aligned with the body and neck components so as to ensure proper final assembly. Without this alignment, the stem may be off axis, making it difficult or impossible to assemble the neck and body segments along an axis.

Other methods for implanting two-piece or three-piece modular devices where the stem component is separate from the body and/or neck component(s) include inserting the stem component until it is proud of its intended final position and then using the body component to seat the stem by impaction. For example, a two-piece system having separate stem and combination body/neck components is manufactured and sold by the Biomet Corporation, under the "Impact Hip System" tradename. For further example, a three-piece system having separate stem, body, and neck components is manufactured and sold by the Exactech Corporation, under the "Accumatch M-Series Hip System" tradename. In both examples, impaction of the body onto the stem also serves to secure the stem and body assembly. One disadvantage of this method is that stem/body orientation must be determined visually prior to full seating and may shift during implantation. Another disadvantage is that the assembly force is equivalent to the resistance of the stem sliding down the canal. If the stem moves in the canal during final assembly, the stem may be driven too deeply into the canal causing surgical delays, or the stem and body will not be tightly assembled, leading to fretting, corrosion, and early failure of the construct.

SUMMARY OF THE INVENTION

An object of the invention is to provide an instrument for inserting a modular implant in which the instrument allows the rotational positioning of the body component, neck component and stem component relative to one another.

Another object of the invention is to provide an instrument for inserting a modular implant which allows rotational positioning of a neck and body component relative to a stem component.

A further object of the invention is to provide a system for inserting a modular implant in which the insertion tool provided with the body component and the stem component allows positioning of the body component and the stem component relative to one another.

With the above and other objects in view, as will hereinafter appear, there is provided an instrument for inserting a modular implant, the instrument comprising a first end and a second end, the first end having engagement means for engaging a stem component of the modular implant, the engagement means comprising separation means for separating a body component of the modular implant and the stem component from one another so as to permit rotational positioning of the body component and the stem component relative to one another.

This invention provides for an improved apparatus and method of inserting or implanting a modular orthopedic prosthesis. The improved apparatus and method allows the components of the implant to be assembled together and inserted into the femur without the need for the modular connections to be locked together, thereby permitting each component to seek its best fitting position within the canal. Further, this permits the orientation of the neck component relative to the body and stem after they have achieved this best fitting position. The implant neck, body, and stem may rotate freely with respect to one another until the components are fully seated in the bone. This results in improved alignment between the implant and the bone, which in turn reduces the time and force required to implant the prosthesis. This method may be used in implanting hip, shoulder, and knee prostheses, among other things.

In accordance with a further feature of the invention there is provided a system for inserting a modular implant, the system comprising: a body component having a neck segment extending therefrom, and the body component forming a bore and counterbore therein; a stem component having a threaded end configured for selective disposal within the bore and counterbore so as to expose through the counterbore a given length thereof; and an insertion tool comprising a first end and a second end, the first end forming a threaded recess for engaging the stem component of the modular implant, the threaded recess having a depth less than the length of the threaded end so as to permit rotational positioning of the body component and the stem component relative to one another.

The present invention improves upon existing techniques by allowing for the complete (fully seated) implantation of the stem and body while maintaining rotational freedom between the stem, body, and neck components. Alternatively, the surgeon may elect to assemble the neck and body at the desired orientation as determined during the trialing phase of surgery. A method of a preferred embodiment of the present invention allows for the stem to be held securely during insertion, while the neck and body assembly may rotate freely about the stem positioning in order to seat the stem in a best fitting position. Once the body is fully seated, the driver may be removed and the implants may be fully assembled using an assembly tool or another instrument. The present invention is not limited to the use of three-piece designs. The present invention may be used in a two-piece design where the neck and body portions of the implant are manufactured as a one-piece component.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
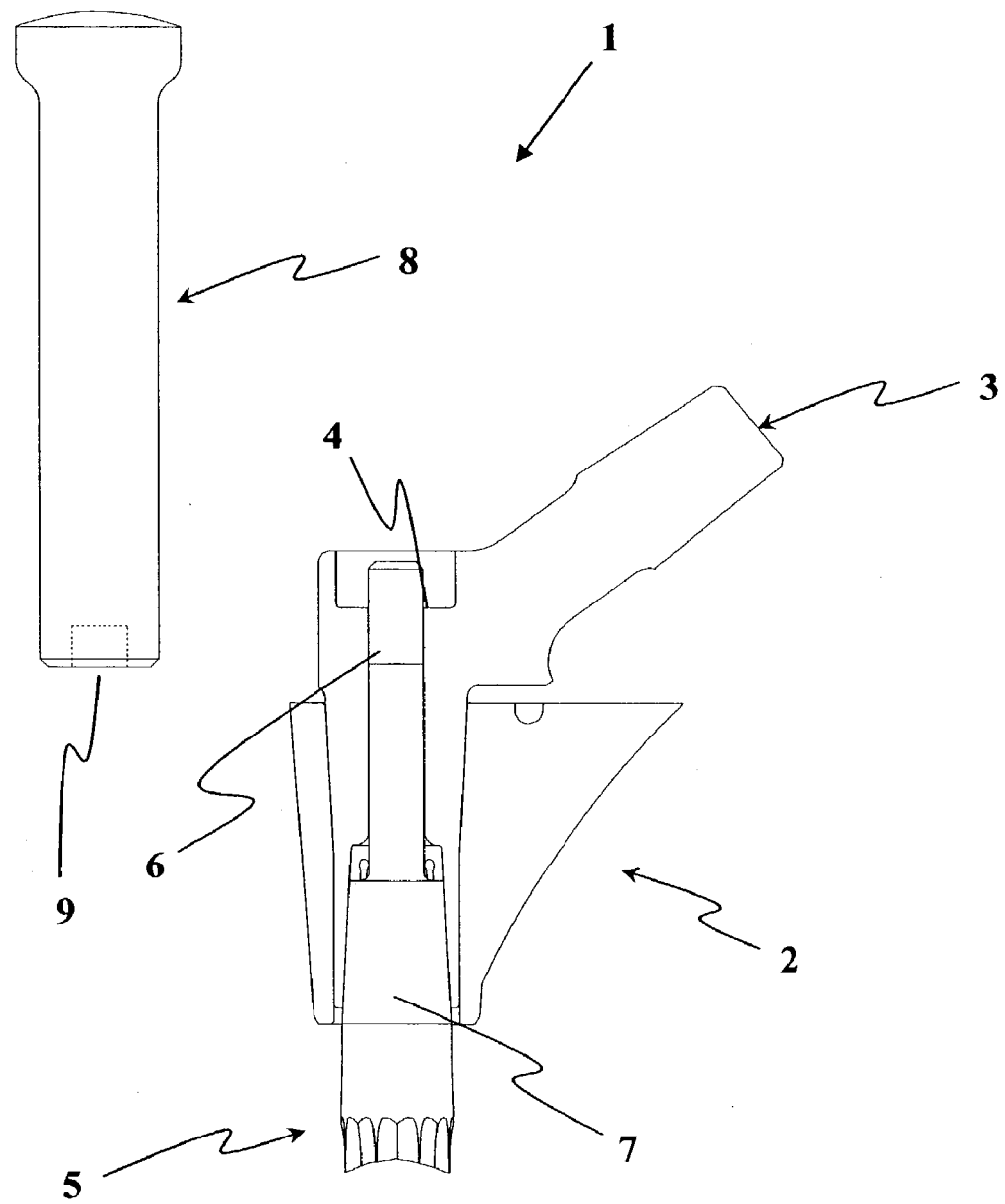
FIG. 1 is a schematic illustration of one form of a modular implant system including a modular implant and an insertion tool.

Referring to FIG. 1, and in a preferred embodiment of the present invention, there is shown a three-piece modular implant system 1. This three-piece modular implant of modular implant system 1 comprises a body segment 2, a neck segment 3 with a counterbore 4, and a stem segment 5 with a threaded end 6 and a taper 7. Threaded end 6 has a length to extend above the surface of counterbore 4 by a predetermined distance. Modular implant system 1 further comprises an insertion tool 8 with threaded hole 9. Hole 9 has a shorter depth than the predetermined distance of threaded end 6 extending above the surface of counterbore 4. Accordingly, when insertion tool 8 is threaded onto threaded end 6 a gap remains between the proximal surface of counterbore 4 and the distal end of insertion tool 8. When the proximal end of insertion tool 8 is impacted, taper 7 is forced out of engagement with the mating surface of body segment 2 so that neck segment 3 remains rotationally free.

Figure 2:
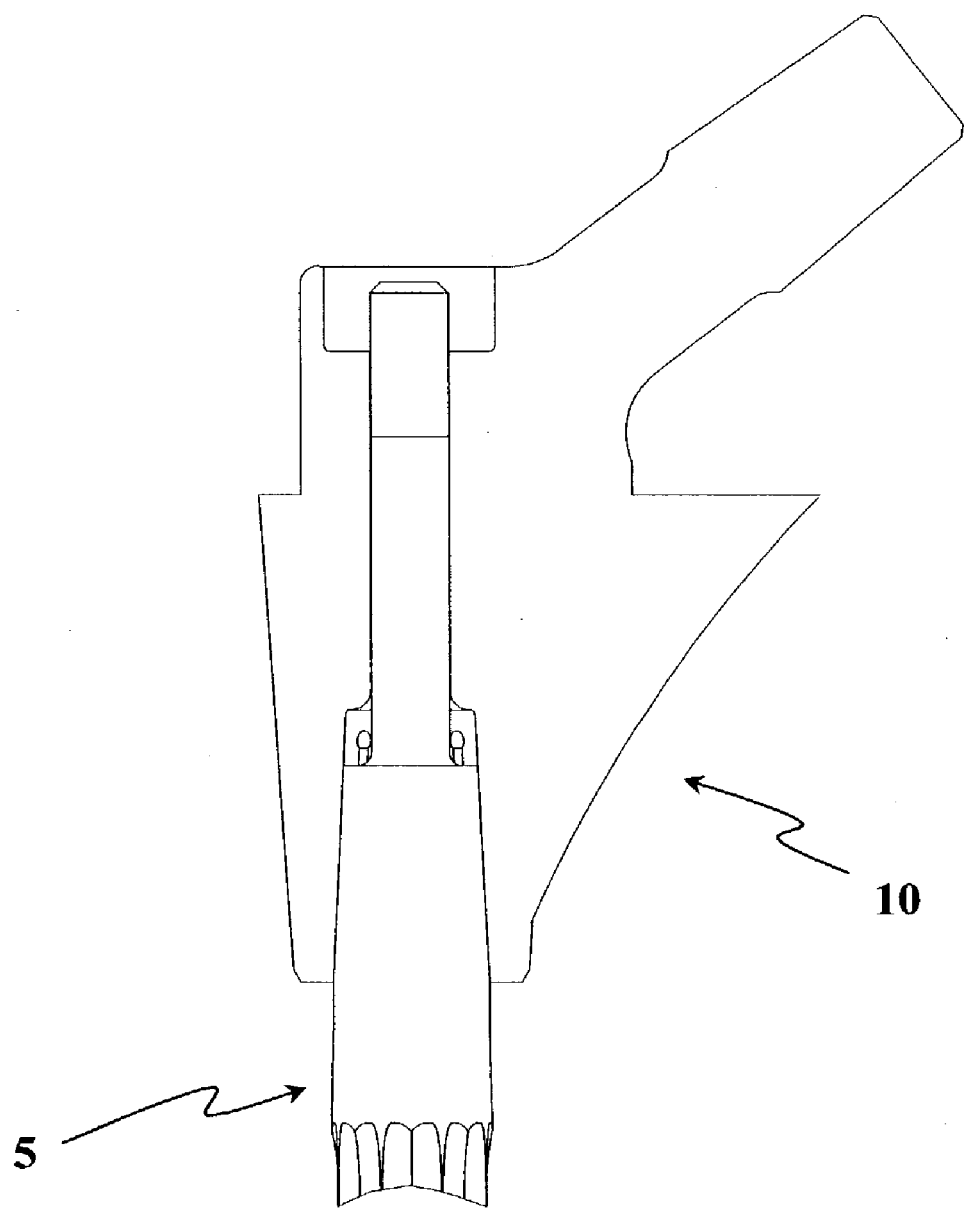
FIG. 2 is a schematic illustration of another form of a modular implant system including a unitary body/neck component for use with the insertion tool.

In another preferred embodiment of the present invention (FIG. 2) there is provided a unitary component comprising a modular body/neck component 10 and a modular stem component 5.

What is claimed is:

1. A multi-component modular joint prosthesis system comprising:
   a body segment provided with a bore extending completely therethrough;
   a neck segment comprising a projection that is slidably received in the body segment bore and is provided with a counterbore extending completely therethrough;
   a stem segment constructed so that when in a first, extended position within the neck segment counterbore, said body segment and said neck segment are locked against rotation relative to one another, and when said stem segment is in a second, retracted position within the neck segment counterbore, said body segment and said neck segment are not locked against rotation relative to one another; and
   an insertion tool for selective attachment to said stem segment, such that when said insertion tool is attached to said stem segment, said stem segment is free to assume a first, extended position or a second, retracted position, and when said insertion tool is attached to said stem segment and said stem segment is in the first, extended position within the body segment bore, such that said body segment and said neck segment are locked against rotation relative to one another, said insertion tool is movable to drive said stem segment from the first, extended position to the second, retracted position, whereby to permit said body segment and said neck segment to rotate relative to one another.

2. A multi-component modular joint prosthesis system according to claim 1 wherein said body segment further comprises a body portion and a neck portion.

3. A multi-component modular joint prosthesis system according to claim 1 wherein said stem segment is provided with tapered walls.

4. A multi-component modular joint prosthesis system according to claim 3 wherein said body segment bore is provided with a tapered portion, and said neck segment is provided with tapered walls adjacent to the body segment bore tapered portion.

5. A multi-component modular joint prosthesis system according to claim 1 wherein said insertion tool is provided with a threaded hole, and said stem segment is provided with a threaded end portion.

6. A multi-component modular joint prosthesis system according to claim 5 wherein the depth of the threaded hole is shorter than the length of said stem segment threaded end portion, such that when the threaded end portion is fully seated in the threaded hole, a gap remains between a proximal surface of said neck segment and a distal surface of said insertion tool.

7. A method for inserting a multi-component modular joint prosthesis comprising:

providing a body segment provided with a bore extending completely therethrough, a neck segment comprising a projection slidably received in the body segment bore and provided with a counterbore extending completely therethrough, a stem segment constructed so that when in a first, extended position within the neck segment counterbore, the body segment and the neck segment are locked against rotation relative to one another, and when in a second, retracted position within the neck segment counterbore, the body segment and the neck segment are not locked against rotation relative to one another, and an insertion tool for selective attachment to the stem segment, such that when the insertion tool is attached to the stem segment, the stem segment is free to assume either a first, extended position or a second, retracted position, and when the insertion tool is attached to the stem component and the stem component is in the first, extended position within the neck segment counterbore bore, such that the body segment and the neck segment are locked against rotation relative to one another, the insertion tool may be used to drive the stem segment from the first, extended position to the second, retracted position, whereby to permit the body segment and the neck segment to rotate relative to one another;

assembling the body segment and the neck segment and the insertion tool so that the insertion tool is attached to the stem segment, and the body segment and the neck segment are not locked against rotation relative to one another;

inserting the prosthesis into a bone;

arranging the body segment and the neck segment into desired positions; and removing the insertion tool, whereby the body segment and the neck segment may be locked into the desired positions.

8. A method according to claim 7 wherein the body segment further comprises a body portion and a neck portion.

9. A method according to claim 7 wherein the stem segment is provided with tapered walls.

10. A method according to claim 9 wherein the body segment bore is provided with a tapered portion, and the neck segment is provided with tapered walls adjacent to the body segment bore tapered portion.

11. A method according to claim 7 wherein the insertion tool comprises a threaded hole, and the stem segment is provided with a threaded end portion.

12. A method according to claim 11 wherein the depth of the threaded hole is shorter than the length of the stem segment threaded end portion, such that when the threaded end portion is fully seated in the threaded hole, a gap remains between a proximal surface of the neck segment and a distal surface of the insertion tool.

* * * * *